(12) United States Patent
Hayashi et al.

(10) Patent No.: US 7,839,068 B2
(45) Date of Patent: Nov. 23, 2010

(54) FLUORESCENT LAMP CAPABLE OF SLOW RELEASE OF ORGANIC EVAPORATING MATERIALS AT LOW TEMPERATURE

(75) Inventors: Daiyu Hayashi, Aachen (DE); Michiel Jacobus Van Der Meer, Wouw (NL); Olaf Mastenbroek, Goes (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 708 days.

(21) Appl. No.: 11/718,404

(22) PCT Filed: Nov. 2, 2005

(86) PCT No.: PCT/IB2005/053567

§ 371 (c)(1),
(2), (4) Date: May 2, 2007

(87) PCT Pub. No.: WO2006/051444

PCT Pub. Date: May 18, 2006

(65) Prior Publication Data

US 2009/0051263 A1 Feb. 26, 2009

(30) Foreign Application Priority Data

Nov. 9, 2004 (EP) .................................. 04105618

(51) Int. Cl.
*H01J 1/62* (2006.01)
(52) U.S. Cl. .................... 313/489; 422/186; 427/67
(58) Field of Classification Search ............... 313/422, 313/493, 634, 507, 484–485, 514–515, 519, 313/633, 631, 489, 491, 483, 475, 473, 56, 313/169.4, 623, 627–643, 567, 111–117, 313/25–27, 318.01–318.09; 439/615, 739; 445/24, 26, 22, 29
See application file for complete search history.

(56) References Cited

U.S. PATENT DOCUMENTS 3,725,311 A * 4/1973 Grubb ......................... 512/4

(Continued)

FOREIGN PATENT DOCUMENTS

EP 0825634 1/2002

(Continued)

*Primary Examiner*—Nimeshkumar D Patel
*Assistant Examiner*—Donald L Raleigh

(57) ABSTRACT

The present invention relates to a fluorescent lamp including a visible radiation and/or UV-radiation transmissive discharge vessel, at least one luminescent layer coated onto the inner wall of the discharge vessel for converting UV-radiation to other wavelengths of UV-A, UV-B and/or visible radiation characterized in, that at a section to which no luminescent layer is applied on the inner surface area of said discharge vessel at least one substrate layer is applied on the outer surface of this area of said discharge vessel, and/or at least a section to which luminescent layer is applied on the inner surface area of said discharge vessel at least one substrate layer is applied on the outer surface of this area of said discharge vessel; whereby said substrate layer comprises at least one volatile organic material being releasable over an extended time period, whereby the volatile organic material is released by UV-radiation and/or thermal heat generated from said fluorescent lamp and, whereby at operation the temperature of the outer surface of the discharge vessel of said fluorescent lamp is $\leq 70°$ C.

16 Claims, 2 Drawing Sheets

U.S. PATENT DOCUMENTS

| | | | | |
|---|---|---|---|---|
| 3,763,347 | A | * | 10/1973 | Whitaker .................. 392/391 |
| 4,099,090 | A | * | 7/1978 | Corth et al. ................ 313/487 |
| 4,184,099 | A | * | 1/1980 | Lindauer et al. ........... 313/315 |
| 6,024,929 | A | * | 2/2000 | Ichikawa et al. ........... 422/186 |
| 6,191,539 | B1 | * | 2/2001 | Green ....................... 315/249 |
| 2004/0213899 | A1 | * | 10/2004 | Wang ......................... 427/67 |
| 2004/0226813 | A1 | * | 11/2004 | Wang ....................... 204/157.3 |

FOREIGN PATENT DOCUMENTS

| | | |
|---|---|---|
| JP | 0814063 | 6/1996 |
| JP | 11054088 | 2/1999 |

* cited by examiner

FLUORESCENT LAMP CAPABLE OF SLOW RELEASE OF ORGANIC EVAPORATING MATERIALS AT LOW TEMPERATURE

The present invention relates to a fluorescent lamp capable of slow release of volatile materials, such as perfumes, deodorants, insecticides, bactericides, pharmaceuticals, antiallergics, at low temperature as well as to the use of said fluorescent lamps.

In the field of lighting equipment, techniques of high temperature induced release of volatile ingredients are disclosed in U.S. Pat. No. 4,184,099.

In the above-mentioned U.S. Pat. No. 4,184,099, bodies which are formed compositions of Versalon® type polyamide resin containing from about 35% up to about 70% by weight of highly volatile materials such as perfumes, deodorants, insecticides, bactericides, and animal repellents which are able to act in a very diluted vapor state in the air for relatively long periods of time, are described. The highly volatile substances are released in a controlled manner over a long period of time. The molecular weight of the resin is between 9,000 and 12,000, and its softening point varies from 120° C. up to 400° C. In addition, articles are described incorporating said composition and, as part of the instant invention, a light bulb coated with a toroidal article which consists essentially of said composition, is disclosed.

However, U.S. Pat. No. 4,184,099 is not confronted with the object to provide slow release of volatile materials at low temperatures. Moreover, U.S. Pat. No. 4,184,099 does not directed to fluorescent lamp, which are known to have a much lower operation temperature compared to prior art light bulbs.

Further, U.S. Pat. No. 4,184,099 is silent to the problem how a more or less continuous slow release of volatile materials at low temperatures can be obtained and/or a desired release rate of volatile materials at low temperatures can be adjusted over a long period of time.

Also, U.S. Pat. No. 4,184,099 is not confronted with the object to provide a specific room concentration in a defined area surrounding the fluorescent lamp in order to mask an unpleasant odor near to the fluorescent lamp without significantly changing the ambient air in a distance there from.

In addition, a drawback of temperature induced release of volatile ingredients, in particular of high temperature induced release as described in U.S. Pat. No. 4,184,099 is, that it takes some time to cool down the light bulb, when switch off, to ambient room temperature. Thus, volatile ingredients are released to some extend during that time period of cooling down although the light bulb has been already switched off.

Another drawback is, that at high operation temperatures typically for light bulbs volatile ingredients can decompose, which can cause a burning or unpleasant smell.

Therefore, an object of the present invention is to overcome at least one disadvantage mentioned above.

Further, it is an object of the present invention to release volatile materials at low temperatures induced by a fluorescent lamp.

Another object of the present invention is to release volatile materials induced by a fluorescent lamp at low temperatures in a predefined amount over a long period of time.

Another object of the present invention is to release volatile materials induced by a fluorescent lamp at low temperatures during operation of the fluorescent lamp only.

To attain at least one of the mentioned objects above, the present invention provides a fluorescent lamp including a visible radiation and/or UV-radiation transmissive discharge vessel, at least one luminescent layer coated onto the inner wall of the discharge vessel for converting UV-radiation to other wavelengths of UV-A, UV-B and/or visible radiation, whereby at a section to which no luminescent layer is applied on the inner surface area of said discharge vessel at least one substrate layer is applied on the outer surface of this area of said discharge vessel; and/or at least a section to which luminescent layer is applied on the inner surface area of said discharge vessel at least one substrate layer is applied on the outer surface of this area of said discharge vessel;

whereby said substrate layer comprises at least one volatile organic material being releasable over an extended time period, whereby the volatile organic material is released by UV-radiation and/or thermal heat generated from said fluorescent lamp and, whereby at operation the temperature of the outer surface of the discharge vessel of said fluorescent lamp is $\leq 100°$ C.

Most preferred, at operation the temperature of the outer surface of the discharge vessel of said fluorescent lamp is $\leq 70°$ C.

A fluorescent lamp according to the present invention can be a fluorescent gas discharge lamp, preferably a mercury discharge lamp and more preferred a low-pressure mercury vapor discharge lamp. Most preferred the fluorescent lamp according to the present invention can be any fluorescent lamp generating UV-radiation, which can be converted to other wavelengths, for example to UV-A and/or UV-B for tanning purposes or to visible radiation for general lightning purposes. Fluorescent lamps according to the present invention can be used for general lightning purposes, for tanning purposes, in particular as sun bed lamps, for room freshening purposes, for malodor reduction, for medical purposes, for sanitary purposes, for antiallergic purposes, disinfection purposes and/or insect trap purposes.

A fluorescent lamp usable according to the present invention can comprise a discharge vessel having one or at least two end portions, wherein an electrode carrier is arranged in an end portion, which electrode carrier carries an electrode for generating and maintaining a discharge in the discharge vessel.

In a fluorescent lamp mercury is the primary component for generating ultraviolet (UV) light. However, said fluorescent lamp can also be mercury free but instead contains components which generates IN-radiation. These components or also called "ionisable fillings" to generate UV-radiation are general known to the expert.

The fluorescent lamp further comprises a buffer gas, such as inert gas, preferably selected from the group comprising neon, argon, krypton, xenon, etc.

The inner wall of the discharge vessel may be coated with a luminescent layer comprising a luminescent material, for example a fluorescent powder for converting UV-radiation to the desired radiation.

Preferably, the fluorescent lamp is a low-pressure discharge lamp. However, it is preferred that the discharge vessel and/or the fluorescent lamp usable according to the present invention is substantially circular in cross-section. The shape of the discharge vessel and/or the fluorescent lamp can be tube like or bulb like.

To efficiently enhance the UV-activated release of volatile organic material it is provided at least one area of the inner surface of the discharge vessel onto which no luminescent material is applied, so that due to degradation of said substrate layer, which is placed at least opposite to said area onto the upper outer surface of said discharge vessel, entrapped volatile organic material is slowly released.

The substrate layer comprising a volatile organic material can be applied in various manners on the outer upper surface of the discharge vessel. For example, the substrate layer can be applied such that the outer upper surface of the discharge vessel is partly or completely covered by said substrate layer. It is preferred that the substrate layer is circumference applied to the outer upper surface of the discharge vessel.

It is preferred that the substrate layer is transmissive and/or transparent for visible radiation and/or UV radiation. A transmissive and/or transparent substrate layer can be colorless or practically colorless. It can be also desired that the transmissive and/or transparent substrate layer is colorful. However, the substrate layer can be of course non- or practically non-transmissive and/or non-transparent for visible radiation and/or UV radiation. In particular, if the substrate layer is partly covered by said substrate layer, it can be preferred that the substrate layer is non- or practically non-transparent for visible radiation and/or UV radiation. For example, if to a part to which no luminescent layer is applied on the inner surface area of the discharge vessel substrate layer is applied on the outer surface thereto, it can be advantageously that the substrate layer is non- or practically non-transparent for UV-radiation in order to avoid an unwanted UV-radiation to the environment, especially to consumer.

The word "transparent" means that an object on one side of the substrate layer is visible by viewing from the other side of the substrate layer with a naked-eye.

It can be preferred that a transmissive and/or transparent substrate layer comprising volatile material is able to transmit radiation with a wave length in the range of 200 nm-1200 nm. In particular, it can be desirable that the transmissive and/or transparent substrate layer transmits radiation with a wave length in the range of 290 nm-750 nm, preferably radiation with a wave length in the range of 325 nm-388 nm or at least above 365 nm, more preferred with a wave length in the range of 405 nm-436 nm. It can be desired further that the substrate layer transmits more than 50%, preferably more than 60%, further preferred more than 70%, more preferred more than 80% and most preferred more than 90% of radiation with a wave length range of 290 nm-750 nm.

According to an embodiment of the present invention, between the substrate layer and the outer upper surface of the discharge vessel at least one layer free of volatile organic material can be arranged, for example to reduce the temperature, UV-activity etc.

It is an aim of the present invention to provide at low temperature a release, preferably slow release, of volatile organic material to the environment. Moreover, it is preferred that the release of volatile organic material can be effected over an extended time period of at least 50 hours. According to the present invention it can be preferred that the extended time period of release is about of at least 100 hours, preferably 250 hours, more preferably 500 hours, and most preferably up to 15,000 to 20,000 hours or more, based on operation time of the fluorescent lamp according to the present invention.

With respect to tanning lamps or sun bed lamps according to the present invention it is preferred that the time period of release is about of at least 300 to 1,000 hours, preferably 400 to 800 hours and more preferably 450 to 650 hours, based on operation time of the lamp.

At operation the temperature of the outer surface of the discharge vessel of said fluorescent lamp is preferably $\leq 70°$ C. and $\geq$room temperature, more preferably $\leq 65°$ C. and $\leq 60°$ C. and most preferably $\geq 40°$ C. and $\leq 55°$ C.

It is an advantage of the fluorescent lamp according to the present invention that due to the lower operation temperature thereof a release of volatile organic material can be dramatically reduced compared to light bulbs when switch off. Thus, a release of volatile organic material can be effected at operation but more or less immediately reduced to significant low level at a switch off state.

It can be further preferred that the release of the volatile organic material is over a wide time period at operation of the fluorescent lamp according to the present invention is more or less constant. To achieve a substantially constant release of volatile organic material at operation of the fluorescent lamp according to the present invention a variety of structural measurements of the substrate layer can be made.

To provide a slow release rate of the volatile material, the volatile material can be encapsulated. For example, the substrate layer can be made of an encapsulated volatile material and or the encapsulated volatile material can be embedded into the substrate layer. Further, it can be preferred to use a porous carrier comprising a volatile material and/or a porous substrate layer comprising the volatile material to provide a slow release of the volatile material at low temperature over a long period of time. In combination or as an alternative a barrier layer can be used to provide a slow release rate of volatile material. It is preferred that the barrier layer is applied on top of a substrate layer. However, the barrier layer can be a luminescent layer, preferably a transparent luminescent layer.

Further, an UV-protecting layer can be used on a fluorescent lamp according to the present invention, for example on top of an surface of a substrate layer, on top of a surface of a barrier layer and/or between said substrate layer and said barrier layer in order to avoid a short wave UV-radiation which could be harmful. An UV-protecting layer can be advantageously used to outwardly cover these areas of the discharge vessel to which an inner luminescent layer is not applied.

The volatile material can be adsorbed onto a carrier, which ensures both the fine distribution of the perfumes in the substrate layer and controlled release during operation of the fluorescent lamp according to the present invention. Such carriers can be porous inorganic materials such as light sulfate, silica gels, zeolites, preferably zeolites of Type A, X or Z, gypsums, clays, granulated clays, aerated concrete etc. or organic materials such as wood and cellulose-based materials.

The volatile material can also be in microencapsulated or spray-dried form or in the form of inclusion complexes.

The substrate layer comprising volatile material can be in the form of extrusion products and they can be applied in this form to the outer surface of the discharge vessel of the fluorescent lamp.

Possibly, the properties of the volatile material modified in the above manner can be further optimized by so-called "coating" with suitable materials for the purpose of the more systematic release of the volatile material concerned, for which purpose, wax like plastics such as, for example, polyvinyl alcohol are preferably used. The microencapsulation of the volatile material can, for example, be carried out by the so-called coacervation process with the aid of capsule materials of, for example, polyurethane-like materials or soft gelatins. Spray-dried volatile material can for example be prepared by spray-drying an emulsion or dispersion containing the composition. As carries modified starches, proteins, dextrin and/or vegetable gums can be used. Inclusion complexes can be prepared, for example, by introducing dispersions of the composition and cyclodextrine or urea derivatives into a suitable solvent, such as for example water. Extrusion products can be prepared by melting the volatile material with a suitable waxlike substance and by extrusion followed by solidification, optionally in a suitable solvent, such as for example isopropanol.

This coating prevents the volatile material from diffusing out of the particles. Moreover, the coating helps preserve the original "character" of volatile material, such as perfumes having particularly volatile top-notes.

The coating materials used herein is preferably degradable by UV-radiation, and are designed to break-up in an amount as the volatile material is needed, thereby releasing the volatile material.

The particles may be coated with more than one UV-degradable material to produce a particle having more than one layer of coating. Different coating materials can be chosen to provide different volatile material protection as needed, so long as one of the coatings, generally, the outermost, is UV-degradable.

The individual volatile material containing particles may also be agglomerated with the coating material to provide larger particles, which comprise a number of the individual volatile material containing particles. This agglomerating material surrounding the particles provides an additional barrier to diffusion of the volatile material out of the particles. Such an approach also minimizes the surface area of free particles susceptible to volatile material diffusion. The ratio of volatile material particles to agglomerate material will vary greatly depending upon the extent of additional protection desired. This agglomeration approach may be particularly useful with very volatile material or volatile material that are especially susceptible to degradation. Also, agglomeration of very small volatile material particles would provide additional protection against premature diffusion out of volatile material.

The porous carrier, porous substrate layer and/or barrier layer can have pores of a diameter of 1 nm to 100 µm, preferably is 200 nm to 50 µm. However, the porous carrier, porous substrate layer and/or barrier layer can have pores of a diameter of 10 nm to 90 µm, 50 nm to 80 µm or 100 nm to 60 µm. The diameter of the pores should preferably be selected such that volatile material can slowly penetrate therethrough at operation of the fluorescent lamp according to the present invention. However, the carrier material, substrate layer and/or barrier layer can be selected so, that pores are formed due to UV-radiation, i.e. UV-actuated degradation of carrier material, substrate layer and/or barrier layer.

According to the present invention it can be preferred to decrease the release rate of the volatile material at low temperature by adding a retaining agent to the volatile material and/or substrate layer. In general, all retaining agents are suitable which can reduce the release rate of the volatile material. A retaining agent can be selected from the group comprising a gel, a wax, an adhesive, a resin and/or a component with a high viscosity. However, a gel and/or tackifying agent are most preferred.

Further, it can be preferred that the substrate layer allows for diffusion of the perfume therethrough, if the release of the volatile material is heat actuated. However, a substrate layer, which is poorly or non permeable for volatile material can be used. Due to UV-radiation a degradation of the substrate layer can be achieved, so that volatile material can be released depending on the rate of degradation of the substrate layer. Also, the volatile material can be chemically bonded to the substrate layer, whereby the bond between volatile material and the substrate layer is UV-labile. Due to UV-radiation bond-breaking of said UV-labile bond can be achieved, so that the volatile material is released from the substrate to the environment at operation of a fluorescent lamp according to the present invent. The substrate layer is in general an organic material, whereby the organic material is selected from the group comprising polymer, wax, saccharide, resin and/or adhesive, preferably the substrate layer is an organic UV-degradable material.

According to the present invention polymers can be preferably used as a substrate layer. Suitable polymers can be selected from the group comprising polyester, polyether, polyamide, polyimide, polyurea, polyurethane, polyethylene, polyacrylate, polyacrylamide, polyvinylacetate, polyethylenimine, polyamine, polyalcohol, polycarbonic acids, elastomer, duromer, saccharide, and/or adhesive.

The molecular weight of the polymers usable according to the present invention can vary in a broad range from a MW of 500 to 10,000,000, preferably 1,000 to 1,000,000, more preferred 2500 to 500,000 and most preferred 5,000 to 50,000. However, polymers with a MW of 10,000 to 25,000 are most preferred.

However, the substrate layer can be a gel or a composition with a high viscosity.

In order to improve the release of volatile material at low temperature over a long period of time the surface of the substrate layer can be important. The amount of released volatile material can be increased by a larger outer upper release surface of the substrate layer. According to the present invention it can be preferred that the total upper outer surface of said substrate layer/s is 1 $mm^2$ to 1500 $cm^2$ and preferably is 6 $mm^2$ to 1000 $cm^2$. However, it can be preferred that the total upper outer surface of said substrate layer/s is 10 $mm^2$ to 700 $cm^2$, 50 $mm^2$ to 500 $cm^2$ or 100 $mm^2$ to 300 $cm^2$.

Further, with respect to heat actuated and/or UV-radiation actuated release of volatile material the surface is as well as the thickness of the volatile material comprising substrate layer may be important. For example, to avoid a high release rate of volatile material actuated by heat, an increased thickness of the substrate layer can be preferred. In case of UV-actuated release of volatile material it can be suitable to use a thin substrate layer in view of UV-absorption. Thus, it is preferred that the mean thickness of said substrate layer/s is 1 µm to 2 cm, preferably is 20 µm to 0.5 cm. However, the mean thickness of said substrate layer/s can be 5 µm to 1 cm, 10 µm to 0.3 cm or 50 µm to 0.1 cm.

However, to further influence the release rate it can be preferred that the volatile organic material is releasable at temperatures $\leq 70°$ C., preferably $\leq 60°$ C. or $\leq 50°$ C.

Further, to influence the release rate of volatile material the substrate layer can comprise the volatile material with a concentration gradient. For example, the concentration of volatile material contained in the substrate layer can increase from the lower upper surface of the substrate layer to the outer upper substrate layer. It is preferred that the lower upper surface of the substrate layer is free or practically free of volatile material where else the middle section of the substrate layer comprises the main amount of volatile material. In order to facilitate the production of said substrate layer it is preferred that the substrate layer comprises at least two to five, preferably three to four substrate layers, whereby the substrate layers can vary in the amount of concentration of volatile material. However, it is preferred that the inner substrate layer comprises a higher concentration of volatile material compared to the outer substrate layer.

The volatile organic material can be selected from the group comprising a perfume, a deodorant, an insecticide, bactericide, a pharmaceutical, antiallergic agent and/or an odor reduction.

Perfumes or odors are used for masking malodors. The properties of neutralizing malodors of the fluorescence lamp according to the present invention is surprising. Malodor occurs frequently in daily life and impairs personal well being, in particular, those of domestic pets, kitchen odors, such as those resulting from the preparation of onions, garlic, cabbage or fish, odors due to tobacco smoke, and in particular, cold tobacco smoke, molds and waste. Such malodors are, for example, those resulting from substances transpired or excreted by humans. In addition, malodors are caused by machines and/or electronic articles, such as lamps for tanning purposes, during operation. These malodors are usually caused by particularly odorous substances which are, however, frequently only present in trace amounts.

In the present context, the term "perfume" means any odoriferous material or any material, which acts as a malodor counteractant. In general, such materials are characterized by a vapor pressure greater than atmospheric pressure at ambient temperatures. The perfume or deodorant materials employed herein will most often be liquid at ambient temperatures, but also can be solids such as the various camphoraceous perfumes known in the art. A wide variety of chemicals are known for perfumery uses, including materials such as aldehydes, ketones, esters and the like. More commonly, naturally occurring plant and animal oils and exudates comprising complex mixtures of various chemical components are known for use as perfumes, and such materials can be used herein. The perfumes herein can be relatively simple in their composition or can comprise highly sophisticated, complex mixtures of natural and synthetic chemical components, all chosen to provide any desired odor.

Typical perfumes herein can comprise, for example, woody/-earthy bases containing exotic materials such as sandalwood oil, civet, patchouli oil and the like. The perfumes herein can be of a light, floral fragrance, e.g., rose extract, violet extract and the like. The perfumes herein can be formulated to provide desirably fruity odors, e.g. lime, lemon, orange and the like. Suitable perfumes include musk ambrette, musk, musk ketone, musk xylol, aurantiol, ethyl vanillin and mixtures thereof.

Most preferred are odors or also called "perfumes". Suitable perfumes can be selected from the group comprising extracts from natural raw materials such as essential oils, resins, balsams, tinctures such as for example ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom;

Further, odors can be used from the group comprising hydrocarbons, such as for example 3-carene; α-pinene; β-pinene; α-terpinene; γ-terpinene; p-cymene; bisabolene; camphene; caryophyllene; cedrene; famesene; limonene; longifolene; myrcene; ocimene; valencene; (E,Z)-1,3,5-undecatriene; styrene; diphenylmethane; aliphatic alcohols, such as for example hexanol; octanol; 3-octanol; 2,6-dimethyl-heptanol; 2-methyl-2-heptanol, 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; aliphatic aldehydes and their acetals such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanaldiethylacetal; 1,1-dimethoxy-2,2,5-trimethyl-4-hexene; citronellyl oxyacetaldehyde.

Further, odors can be used from the group comprising aliphatic ketones and oximes thereof, such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; aliphatic sulfur-containing compounds, such as for example 3-methylthiohexanol; 3-methylthiohexyl acetate; 3-mercaptohexanol; 3-mercaptohexyl acetate; 3-mercaptohexyl butyrate; 3-acetyltbiohexyl acetate; 1-menthene-8-thiol; aliphatic nitriles, such as for example 2-nonenenitrile; 2-tridecenenitrile; 2,12-tridecenenitrile; 3,7-dimethyl-2,6-octadienenitrile; 3,7-dimethyl-6-octenenitrile.

Further, odors can be used from the group comprising aliphatic carboxylic acids and esters thereof, such as for example (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate.

Further, odors can be used from the group comprising acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien- 1-ol; as well as formates, acetates, propionates, isobutyrates, butyrates, isovalerates, pentanoates, hexanoates, crotonates, tiglinates and 3-methyl-2-butenoates thereof.

Further, odors can be used from the group comprising acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; α-sinensal; β-sinensal; geranylacetone; as well as the dimethyl- and diethylacetals of geranial, neral and 7-hydroxy-3,7-dimethyloctanal.

Further, odors can be used from the group comprising cyclic terpene alcohols, such as, for example, menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates of alpha-terpineol; terpinen-4-ol; methan-8-ol; methan-1-ol; methan-7-ol; borneol; isoborneol; linalool oxide; nopol; cedrol; ambrinol; vetiverol; guaiol.

Further, odors can be used from the group comprising cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-danasceinone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; acetylated cedarwood oil (cedryl methyl ketone).

Further, odors can be used from the group comprising cyclic alcohols, such as, for example, 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol.

Further, odors can be used from the group comprising cycloaliphatic alcohols, such as, for example, alpha,3,3-trimethylcyclo-hexyl-methanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol.

Further, odors can be used from the group comprising cyclic and cycloaliphatic ethers, such as, for example, cineole; cedryl methyl ether; cyclododecyl methyl ether; (ethoxymethoxy) cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-trideca-4,8-diene; rose oxide; 2-(2,4-dimethyl-3-cyclohexen-1-yl)-5-methyl-5-(1-methyl-propyl)-1,3-dioxan.

Further, odors can be used from the group comprising cyclic ketones, such as, for example, 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclo-hexanone; 4-tert.-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadeca-none.

Further, odors can be used from the group comprising cycloaliphatic aldehydes, such as, for example, 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde.

Further, odors can be used from the group comprising cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphtalenyl methyl ketone; methyl-2,6,10-trimethyl-2,5,9-cyclododecatrienyl ketone; tert.-butyl-(2,4-dimethyl-3-cyclohexen-1-yl) ketone.

Further, odors can be used from the group comprising esters of cyclic alcohols, such as, for example, 2-tert.-butylcyclohexyl acetate; 4-tert.-butylcyclohexyl acetate; 2-tert.-pentylcyclohexyl acetate; 4-tert.-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexa-hydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate.

Further, odors can be used from the group comprising esters of cycloaliphatic carboxylic acids, such as, for example, allyl 3-cyclohexyl-propionate; allyl cyclohexyl oxyacetate; methyl dihydrojasmo-nate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol.

Further, odors can be used from the group comprising esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; araliphatic ethers, such as for example 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin.

Further, odors can be used from the group comprising aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4- tert.-butylphenyl)propanal; 3-(4-tert.-butyl-phenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylene-dioxybenzaldehyde; 3,4-dimethoxybenzaldehyde; 2-methyl-3-(4-methoxyphenyl)propanal; 2-methyl-3-(4-methylendioxyphenyl)propanal.

Further, odors can be used from the group comprising aromatic and araliphatic ketones, such as, for example, acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hexamethyl-2-acetonaphthone.

Further, odors can be used from the group comprising aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenyletlcyl cinnamate; cinnamnyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate.

Further, odors can be used from the group comprising nitrogen-containing aromatic compounds, such as, for example, 2,4,6-trinitro-1,3-dimethyl-5-tert-butylbenzene; 3,5-dinitro-2,6-dimethyl-4-tert.-butylacetophenone; cinnamonitrile; 5-phenyl-3-methyl-2-pentenonitrile; 5-phenyl-3-methylpentanonitrile; methyl anthranilate; methyl-N-methylanthranilate; Schiff's bases of methyl anthranilate with 7-hydroxy-3,7-dimethyloctanal, 2-methyl-3-(4-tert.-butylphenyl)-propanal or 2,4-dimethyl-3-cyclohexene carbaldehyde; 6-isopropylquinoline; 6-isobutylquinoline; 6-sec.-butylquinoline; indole; skatole; 2-methoxy-3-isopropylpyrazine; 2-isobutyl-3-methoxypyrazine.

Further, odors can be used from the group comprising phenols, phenyl ethers and phenyl esters, such as, for example, estragole; anethole; eugenol; eugenyl methyl ether; isoeugenol; isoeugenol methyl ether; thymol; carvacrol; diphenyl ether; beta-naphthyl methyl ether; beta-naphthyl ethyl ether; beta-naphthyl isobutyl ether; 1, 4-dimethoxybenzene; eugenyl acetate; 2-methoxy-4-methylphenol; 2-ethoxy-5-(1-propenyl)phenol; p-cresyl phenylacetate.

Further, odors can be used from the group comprising heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4,1-pyran-4-one;

Further, odors can be used from the group comprising lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

It is preferred that the substrate layer comprises the volatile organic material in an amount of 0.01 weight-% to 40 weight-% and preferably of 1 weight-% to 5 weight-%. However, it can be preferred that the substrate layer comprises the volatile organic material in an amount of 0.02 weight-% to 35 weight-%, preferably of 0.05 weight-% to 30 weight-%, more preferably of 0.1 weight-% to 25 weight-% and most preferably of 0.5 weight-% to 10 weight-% and most preferably of 3 weight-% to 8 weight-%.

Hereinafter, details of the present invention will be explained with reference to embodiments shown in the drawings.

Figure 1:
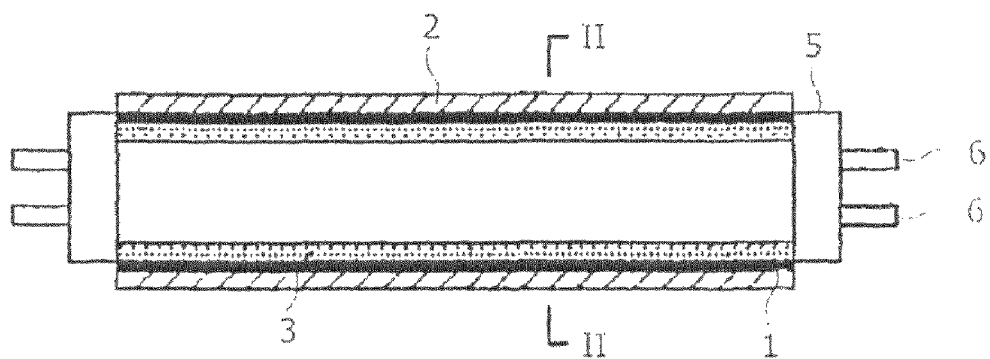
FIG. 1 shows a longitudinal cross-sectional view of a fluorescent lamp.
Figure 2:
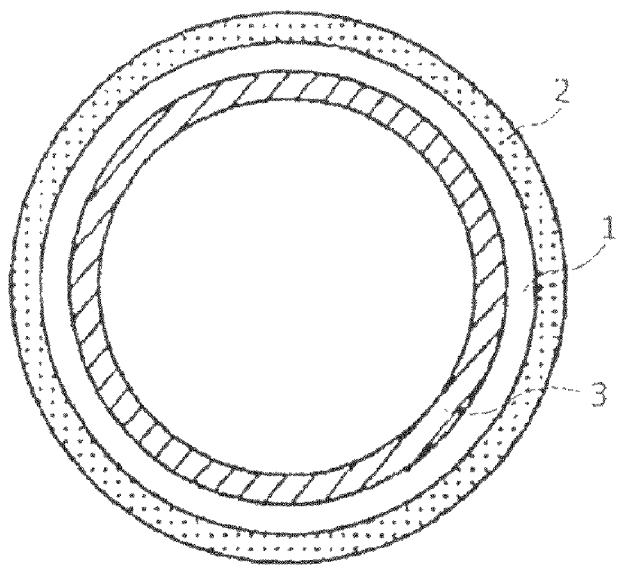
FIG. 2 shows a cross-sectional view fluorescent lamp.

A fluorescent lamp of an embodiment according to the present invention is shown in FIG. 1 and FIG. 2. FIG. 2 is a cross-section of the fluorescent lamp viewed from the position II-II in FIG. 1. The fluorescent lamp possesses a volatile material containing thin composition layer 2 on an outside surface of a straight tube type glass tube discharge vessel 1. A luminescent layer film 3 is coated on an inside surface of the glass tube 1. In the glass tube 1, mercury and buffer gas is enclosed. The electric discharge is generated by electrically connecting the lamp to a power source via bases 5 and pins 6, and the mercury radiates ultraviolet. The luminescent layer film 3 receives the radiated ultraviolet and emits the desired UV-A radiation, UV-B radiation and/or visible light radiation. As the buffer gas, inert gas such as neon, argon, krypton, xenon, and so forth, is used. The thin film composition layer 2 absorbs radiation from the fluorescent lamp, so that volatile material can be released due to UV-radiation and/or heat generated by the fluorescent lamp at operation. Depending on the type of released organic volatile material malodorous substances can be masks, bacteria and fungi can be reduced. Since the thin film composition layer 2 and the thin luminescent layer film 3 neighbor each other via the glass tube discharge vessel 1, the heat of the luminescent lamp according to the present invention and/or the energy of the radiated from the thin film luminescent layer 3 can be efficiently utilized to slow release organic volatile material at low temperatures.

Figure 3:
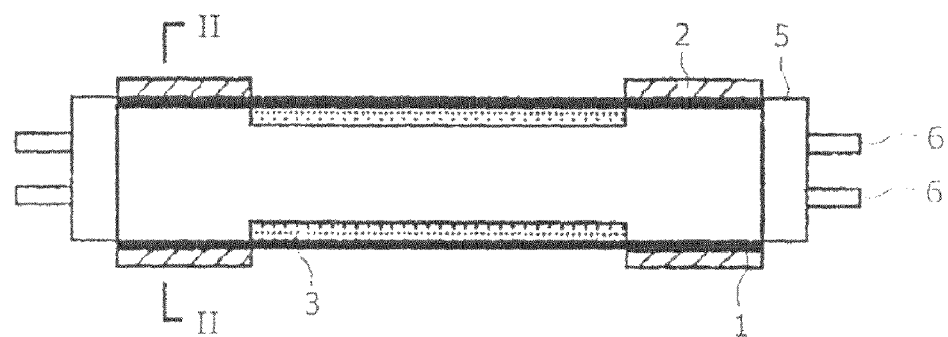
FIG. 3 shows a longitudinal cross-sectional view of a fluorescent lamp.
Figure 4:
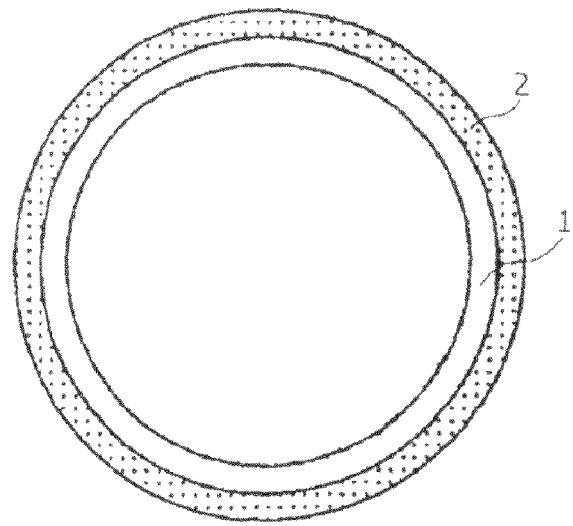
FIG. 4 shows a cross-sectional view fluorescent lamp.

A fluorescent lamp of an embodiment according to the present invention is shown in FIG. 3 and FIG. 4. FIG. 4 is a cross-section of the fluorescent lamp viewed from the position II-II in FIG. 3. The fluorescent lamp possesses a volatile material containing thin composition layer 2 applied to a part on an outside surface of a straight tube type glass tube discharge vessel 1. A luminescent layer film 3 is coated on an inside surface of the glass tube 1 to the sections where the composition layer is not applied. In the glass tube 1, mercury and buffer gas is enclosed. The electric discharge is generated by electrically connecting the lamp to a power source via bases 5 and pins 6, and the mercury radiates ultraviolet. The luminescent layer film 3 receives the radiated ultraviolet and emits the desired UV-A radiation, UV-B radiation and/or visible light radiation. As the buffer gas, inert gas such as neon, argon, krypton, xenon, and so forth, is used. The thin film composition layer 2 absorbs UW-radiation from the fluorescent lamp, so that volatile material can be released due to UV-radiation and/or heat generated by the fluorescent lamp at operation. Depending on the type of released organic volatile material malodorous substances can be masks, bacteria and fungi can be reduced. Since the thin film composition layer 2 and the thin luminescent layer film 3 do not neighbor each other via the glass tube discharge vessel 1, the UV-radiation of the luminescent lamp according to the present invention and/or heat generated at lamp operation can be efficiently utilized to slow release organic volatile material at low temperatures.

Substrate layers comprising volatile material can be obtained by common techniques, for example by blending the volatile material with the substance of the substrate layer followed up by extruding or suchlike, whereby the fluorescence lamp is then coated by the substrate layer containing volatile material.

Coated particles containing volatile material can be obtained by common techniques such as agglomeration techniques, spray drying, fluid bead techniques or such like.

In general, a sun bed with 40 fluorescent lamps are used, each operating at an electrical power of 100 W or 160 W. This results in a UV flux of 30 to 45 UV-Watts per lamp having a UV-B radiation of 0 to 4% and the rest radiation is practically UV-A. The usual radiation lifetime of said tanning lamps is between 500 and 800 hours. The applied aroma is released about the same lifetime. The fluorescent lamps can reach temperatures at operation of about 40° C. (at the ends) to about 90° C. (in the middle). These temperatures largely depend on the electric power and the installed lamp cooling device(s). For the deposition of fragrances containing substrate to the lamp several attempts can be made. A preferred solution is to obtain a fragrance-doped polymer layer of polyethylene or polypropylene shaped to the curvature of the lamp, with a thickness of about 1 mm and a surface of about 15 to 20 cm². Preferably, these fragrance-doped polymer layers can be attached to the fluorescent lamps by use of an adhesive. The temperature to which the fragrances containing substrate is subjected is depending on the position where the fragrances containing substrate is adhered to the lamp. Thus depending on position fragrances containing substrate and the prevailing temperature the amount of fragrance released from the polymer can be altered in order to alter the release rate and release time of the fragrance.

As an alternative, a polymer substrate with a fragrance, for example a low melting polymer, can be melted and/or 'painted' onto the outer upper surface of a fluorescent lamp.

The present invention is further illustrated by example.

To a fluorescent lamp according to FIG. 1 and FIG. 3 having a tubular design operating at an electrical power of 100. W, having a UV flux of 30 to UV-Watts and a UV-B radiation of 0 to 4%, whereby the rest radiation is practically UV-A. A polymer substrate, for example polyethylene or Polyiff®, sold from IFF International Flavors & Fragrances Inc., is applied from the terminal outer upper surface in direction of the center of the fluorescent lamp on both sides of the fluorescent lamp tube, with a thickness of about 1 mm and a surface of about 15 to 20 cm².

The fragrance composition were dispersed in the polymer substrate, for example polyethylene or Polyiff®, in an amount of 10 weight-%, 15 weight-%, 20 weight-% and 25 weight-%, based on the total weight of the polymer substrate.

The fragrance compositions used are listed below.

1. fragrance composition

| | |
|---|---|
| Nonanal | 0.2 weight-%, |
| Decanal | 0.4 weight-%, |
| Benzyl Acetate | 5.0 weight-%, |
| Camphor | 0.4 weight-%, |
| Cineole | 0.4 weight-%, |
| Citral Lemarome | 0.7 weight-%, |
| Geraniol | 5.0 weight-%, |
| Hydroxycitronellal | 2.0 weight-%, |
| Limonene Dextro | 40.0 weight-%, |
| Linalol | 10.0 weight-%, |
| Linalyl Acetate | 16.0 weight-%, |
| Lyral (IFF) | 2.0 weight-%, |
| Methyl Dihydro Jasmonate Super (Q) | 2.0 weight-%, |
| Myrcenyl Acetate | 3.0 weight-%, |
| Terpinyl Acetate | 12.9 weight-%. |

2. fragrance composition

| | |
|---|---|
| Adoxal DEP AA022 | 4 weight-%, |
| Benzyl acetate extra | 7.5 weight-%, |
| Benzyl salicylate | 8 weight-%, |
| Cardamon ceylon A pure | 2 weight-%, |
| Cassis base 345 AB 2967 | 2 weight-%, |
| Cis-3-hexenyl salicylate | 5 weight-%, |
| Citronellol pure | 12 weight-%, |
| Cyclamen aldehyde | 2 weight-%, |
| Dimethyl Benzyl Carbinyl Acetate | 2 weight-%, |
| Geraniol pure | 8 weight-%, |
| Helional | 2 weight-%, |
| Ionone | 6 weight-%, |
| Ligustral | 0.3 weight-%, |
| Lily aldehyde | 6 weight-%, |
| Lyral | 10 weight-%, |
| Mandarinal 32048 SAE | 4 weight-%, |
| Methyl iso eugenol | 3 weight-%, |
| Methyl octyl acetaldehyde | 2.8 weight-%, |
| Ortholate | 3 weight-%, |
| Para cresyl methyl ether | 0.4 weight-%, |
| Phenyl ethyl alcohol | 5 weight-%, and |
| Rosacetone | 5 weight-%. |

3. fragrance composition with insect repellent

30% by weight of the insect repellent of geraniol;
30% by weight of the insect repellent of diethyl phthalate; and
10 weight-% linalol,
10 weight-% limonene,
10 weight-% citronellal,
5 weight-% terpinolene and
5 weight-% p-tertiary butyl cyclohexyl acetate.

4. fragrance composition

| | |
|---|---|
| Dodecanal | 1.25 weight-%, |
| Methylnonyl acetaldehyde | 2.5 weight-%, |
| Allyl amyl glycollate | 1.5 weight-%, |
| Anethole synthetic | 0.2 weight-%, |
| Benzyl salicylate | 15.0 weight-%, |
| Carvone laevo | 0.1 weight-%, |
| Cedramber (IFF) | 4.4 weight-%, |
| Cis-3-hexenyl salicylate | 0.5 weight-%, |
| Citronellol | 2.5 weight-%, |
| Coumarin | 1.0 weight-%, |
| Damascone alpha | 1.0 weight-%, |
| Dihydro myrcenol | 12.0 weight-%, |
| Dipropylene glycol | 6.38 weight-%, |
| Eugenol | 0.8 weight-%, |
| Tonalid (Bush Boake Allan) | 9.0 weight-%, |
| Heliotropin | 0.7 weight-%, |
| Hexyl cinnamic aldehyde | 12.4 weight-%, |
| Lavandin Abrialis | 0.7 weight-%, |
| Lilial (Givaudan-Roure) | 8.0 weight-%, |
| Linalol | 4.0 weight-%, |
| Methyl dihydro jasmonate | 7.0 weight-%, |
| Oakmoss synthetic | 0.3 weight-%, |
| Para t-butyl cyclo hexyl acetate | 6.0 weight-%, |
| Patchouli oil | 2.5 weight-%, |
| Undecalactone gamma | 1.2 weight-%. |

Cedramber, Tonalid and Lilial are all Trade Marks.

5. fragrance composition

| | |
|---|---|
| Nonanal | 0.2 weight-%, |
| Decanal | 0.4 weight-%, |
| Benzyl Acetate | 5.0 weight-%, |
| Camphor | 0.4 weight-%, |
| Cineole | 0.4 weight-%, |
| Citral Lemarome | 0.7 weight-%, |
| Geraniol | 5.0 weight-%, |

-continued

| | |
|---|---|
| Hydroxycitronellal | 2.0 weight-%, |
| Limonene Dextro | 40.0 weight-%, |
| Linalol | 10.0 weight-%, |
| Linalyl Acetate | 16.0 weight-%, |
| Lyral (IFF) | 2.0 weight-%, |
| Methyl Dihydro Jasmonate Super (Q) | 2.0 weight-%, |
| Myrcenyl Acetate 3.0 Terpinyl Acetate | 12.9 weight-%. |

The particular combinations of elements and features in the above detailed embodiments are exemplary only; the interchanging and substitution of these teachings with other teachings in this and the incorporated-by-reference patents/applications are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Further, reference signs used in the description and claims do not limit the scope of the invention as claimed.

The invention claimed is:

1. A fluorescent lamp including a visible radiation and/or UV-radiation transmissive discharge vessel having inner and outer surface areas, at least one luminescent layer applied onto the inner surface area of the discharge vessel for converting UV-radiation to wavelengths of UV-A, UV-B and/or visible radiation, the fluorescent lamp comprising:
    at least one substrate layer applied on the outer surface area of said discharge vessel, said substrate layer comprises at least one volatile organic material being releasable over an extended time period by UV-radiation and/or thermal heat generated from said fluorescent lamp,
    wherein at operation the temperature of the outer surface of the discharge vessel of said fluorescent lamp is ≦100° C., and
    wherein the discharge vessel further comprises:
    at least one first section having the inner surface area coated with the luminescent layer and the outer surface area not coated with the substrate layer; and
    at least one second section having the inner surface area not coated with the luminescent layer and the outer surface area coated with the substrate layer.

2. The fluorescent lamp according to claim 1, wherein the total upper outer surface of said substrate layer/s is 1 mm$^2$ to 1500 cm$^2$.

3. The fluorescent lamp according to claim 1, wherein the mean thickness of said substrate layer/s is 1 µm to 2 cm.

4. The fluorescent lamp according to claim 1, wherein said substrate layer is an organic material selected from the group comprising polymer, wax, saccharide, resin and/or adhesive.

5. The fluorescent lamp according to claim 1, wherein said volatile organic material is selected from the group comprising a perfume, a deodorant, an insecticide, bactericide, a pharmaceutical and/or an antiallergic agent.

6. The fluorescent lamp according to claim 1, wherein said substrate layer comprises the volatile organic material in an amount of 0.01 weight-% to 40 weight-%.

7. The fluorescent lamp according to claim 1, wherein at least one substrate layer comprises particles of coated volatile organic material and/or porous particles containing volatile material.

8. The fluorescent lamp according to claim 1, wherein said substrate layer has a porous structure that comprises pores with a diameter of 1 nm to 100 µm.

9. The fluorescent lamp according to claim 1, wherein onto at least one substrate layer a slow release barrier layer and/or UV-protecting layer is applied.

10. The fluorescent lamp according to claim 1, wherein the fluorescent lamp is a gas discharge lamp selected from one of a mercury discharge lamp and a low-pressure mercury vapor discharge lamp.

11. The fluorescent lamp according to claim 1, wherein the lamp is adapted for use for one or more of general lightning purposes, tanning, sun bed lamps, room freshening purposes, malodor reduction, medical purposes, sanitary purposes, antiallergic purposes, disinfection purposes, and/or insect trap purposes.

12. The fluorescent lamp according to claim 2, wherein the total upper outer surface of said substrate layer/s is 6 mm$^2$ to 1000 cm$^2$.

13. The fluorescent lamp according to claim 3, wherein the mean thickness of said substrate layer/s is 20 µm to 0.5 cm.

14. The fluorescent lamp according to claim 4, wherein the substrate layer is an organic UV-degradable material.

15. The fluorescent lamp according to claim 6, wherein said substrate layer comprises the volatile organic material in an amount of 1 weight-% to 5 weight-%.

16. The fluorescent lamp according to claim 8, wherein said substrate layer comprises pores with a diameter of 20 nm to 50 µm.

* * * * *